US006551556B1

United States Patent
Park et al.

(10) Patent No.: US 6,551,556 B1
(45) Date of Patent: Apr. 22, 2003

(54) AUTOMATIC DNA PURIFICATION APPARATUS

(75) Inventors: Han-Oh Park, Chungcheongbukdo (KR); Han-Ee Park, Chungcheongbukdo (KR); Nam-Sun Kwon, Chungcheongbukdo (KR); In-Suk Joung, Chungcheongbukdo (KR)

(73) Assignee: Biioneer Corporation, Chungcheongbukdo (KR)

( * ) Notice: Subject to any disclaimer, the term of this patent is extended or adjusted under 35 U.S.C. 154(b) by 50 days.

(21) Appl. No.: 09/676,505

(22) Filed: Oct. 2, 2000

(30) Foreign Application Priority Data

| Oct. 2, 1999 | (KR) | 99-42455 |
| Mar. 24, 2000 | (KR) | 00-15206 |
| Sep. 23, 2000 | (KR) | 00-56037 |

(51) Int. Cl.⁷ .................................................. B01L 3/00
(52) U.S. Cl. ........................ 422/99; 422/65; 435/6; 435/41; 435/270
(58) Field of Search ............... 422/99, 65; 210/321.75; 435/6, 41, 270

(56) References Cited

U.S. PATENT DOCUMENTS

| 3,883,305 A | * 5/1975 | Hoskins et al. ............... 422/65 |
| 5,330,914 A | * 7/1994 | Uhlen et al. ................. 435/270 |
| 5,451,500 A | * 9/1995 | Stapleton ...................... 435/6 |
| 5,645,723 A | * 7/1997 | Fujishiro et al. ........ 210/321.75 |
| 6,136,555 A | * 10/2000 | Jones ........................... 435/41 |

OTHER PUBLICATIONS

Holmes et al., Anal. Biochem., 114, 193–197 (1981).
Marko et al., Analytical Biochemistry, 121, 382–387 (1982).
Vogelstein et al., Proc. Natl. Acad. Sct. USA, vol. 76, No. 2, 615–619 (1979).
Buffone et al., Clin. Chem., 27/11, 1945–1949 (1991).
10–2000–0054999, Verified English Translation of Abstract.
10–2000–0055968, Verified English Translation of Abstract.

* cited by examiner

Primary Examiner—Jill Warden
Assistant Examiner—Brian Sines
(74) Attorney, Agent, or Firm—Birch, Stewart, Kolasch & Birch, LLP (57) ABSTRACT

The present invention relates to an automatic DNA isolation apparatus which comprises liquid containers; numerous liquid flow passages; control valves; numerous syringes; numerous injection needles; transportation means; vacuum block; plate rack (31); numerous multi-well plate blocks; and process control unit which regulates the operation of said control valves for selection and transfer of said various liquids, the operation of said syringe for quantitative intake and discharge of said liquids, the transfer of said injection needle connected with said syringes, the sequential transportation of said multi-well plates arranged in said multi-well plate rack, the sequential operation of shaking block and said vacuum block.

5 Claims, 6 Drawing Sheets

AUTOMATIC DNA PURIFICATION APPARATUS

TECHNICAL FIELD

The present invention relates to an automatic DNA purification apparatus and more particularly, to an apparatus for isolating and purifying DNA automatically from various liquids which contain DNA, such as cell culture media.

BACKGROUND ART

As is known, the process for DNA isolation and purification from DNA containing solutions, such as cell culture media, is prerequisite procedure for gene amplification, nucleotide sequence analysis, gene recombination. At present, several conventional methods for isolation and purification of DNA from various biological samples, such as blood, biological tissue, animal cell, plant tissue, E.coli, virus, agarose gel and the like, have been publicly known.

For example, the boiling method (Holms, D. S. and M. Quigley, 1981, Anal. Biochem. 114:193) and the alkaline lysis method (Birnboim, H. C. and J. Doly, 1979, Nucleic Acids Res. 7:1513) have been reported as methods for isolation of plasmid DNA from E.coli and bacterial transformants.

Also, the plasmid DNA purification method which employs CsCl density gradient centrifugation process to obtain high purity DNA, has been reported. However, such method takes a lot of time and in addition, comprises a lot of steps, such as detergent-mediated lysis step, protease treatment step, phenol extraction and ethanol precipitation step. Therefore, such method is not suitable to be employed as a commercial process for the production of high purity DNA in a large scale.

In addition, it has also been reported that the DNA purification method, wherein DNA is adsorbed on the surface of silica or glass in the presence of chaotropic salts, such as NaI or $NaClO_4$ and thereby, isolated from various extracts (Marko, M. A. et al. 1982, A procedure for the large scale isolation of highly purified DNA using alkaline extraction and binding to glass powder. Anal. Biochem. 121:382–387; Vogestein. B. et al. 1979. Preparative and analytical purification of DNA from agarose. Proc. Natl. Acad. Sci. USA. 76:615–619). Such DNA adsorption method in the presence of chaotropic salts, is a general method which isolates and purifies chromosomal DNA or plasmid DNA from cell lysate (Buffone, G. J., et al. 1991. Clin. Chem. 37., 1945).

Such adsorption process is proceeded by using compressed glass fiber or silica particle suspension which contain activated surface on which DNA is adsorbed in guanidine hydrochloride buffer solution with a pH of 4 to 5 or in 4M sodium iodide solution with a pH of 7.5 to 8.

Recently, DNA purification apparatus which can obtain DNA at a time from a large number of biological samples, is required for genome study, blood test, plant seed inspection, agricultural test, microbiological environmental test.

By the way, as mentioned above, although DNA isolation and purification process is a prerequisite step for nucleotide sequence analysis, gene amplification or gene cloning process, the conventional hand-operated DNA purification process is time-consuming and very laborious process and thus, the amount of DNA obtained therefrom varied remarkably depends on operator's mastery.

In order to overcome the above problems, several automatic purification apparatuses have been developed up to now. However, the number of DNA solutions which can be treated at a time in the apparatuses thus developed, is limited. Moreover, DNA cannot be obtained in a large amount within a short time because it is impossible to supply DNA containing solutions continuously and sequentially in such apparatus.

In addition, the conventional DNA purification apparatus is not cost-effective due to the disposable injection tips which should be used for the injection of various solutions and, could not be automated completely on account of filtration and adsorption process.

Therefore, in this technical field, the development of automatic DNA purification apparatus which can isolate and purify DNA simultaneously from a large number of liquids which contain DNA through automatic processes, and which do not use disposable injection tips by employing injection needles which can be used repeatedly, has been desired.

In order to produce such automatic DNA purification apparatus, the injection apparatus which can select liquids from various samples automatically and sequentially and which can control precisely the quantitative injection of the selected liquids, has been desired.

However, the rotary type multi-channel valve has been developed up to present, has some drawbacks, for example, the leakage of liquid in contacting point between each flow passages and the formation of liquid droplet in terminal of outlet, which obstruct seriously accurate quantitative liquid injection. Thus, such type multi-channel valve cannot be employed in an automatic DNA purification apparatus which should control precisely quantitative and selective injection of a large number of liquid in due sequence.

Therefore, the development new type multi-channel quantitative control valve which can minimize the leakage of liquid, and which can accurately control the quantitative injection of liquid by suppressing the formation of liquid droplet in the terminal of flow passage by means of pulse-mode liquid feeding, has been required for the production of high efficient automatic DNA purification apparatus.

In addition, an injection apparatus which can feed various kinds of liquids continuously and in due sequence, is prerequisite for the production of the automatic DNA purification apparatus which can isolate and purify DNA simultaneously from various kinds of liquids which contain DNA through automatic processes.

DISCLOSURE OF INVENTION

Therefore, the objection of the present invention is to provide an apparatus which can isolate and purify DNA in large scale within a short time simultaneously from various liquids which contain DNA.

The above object of the present invention is achieved by providing an automatic DNA purification apparatus, which comprises:

liquid containers (10) which supply various liquid reagents and liquids which contain DNA;

numerous liquid flow passages (21) wherein various kind of liquids stored in said liquid container (10) are conveyed;

control valves (22, 24, 25) which control the selection and transfer of various liquids;

numerous syringes (23) which intake and discharge said various liquids quantitatively;

numerous injection needles (26) which are connected with said numerous syringes (23) respectively through numerous liquid flow passages;

transportation mean (30) for moving said injection needles and/or multi-well plate toward up-down and/or right-left directions;

vacuum block (41) wherein liquids contained in said multi-well plate are filtered in vacuo;

multi-well plate rack (31) which transports said multi-well plates toward up-down directions;

numerous multi-well plate blocks (40) wherein multi-well plates which have been transported through said multi-well plate rack, are mounted;

process control unit(not depicted) which regulates the operation of said control valves for selection and transfer of said various liquids, the operation of said syringes for quantitative intake and discharge of said liquids, the transfer of said injection needles connected with said syringes, the sequential transportation of said multi-well plates arranged in said multi-well plate rack, the sequential operation of shaking block and said vacuum block, according to a computer program.

In addition, the automatic DNA purification apparatus of the present invention may further comprises a washing block (60) which washes said injection needles and/or a shaking block (50) which shake said multi-well plate.

The operation of this apparatus is controlled by said process control unit which instructs, regulates or intermits the sequential proceeding of all operations according to the computer program installed therein in advance. The mechanical operations of this apparatus driven by electric motors, are regulated by electric signal generated from said process control unit. The operations of said control valves and the transfer of liquids are regulated by air pressure generated from air compressor and/or air pump(not depicted) according to electric signals of said process control unit.

Said process control unit is composed of conventional computer equipped with memory units, central processing units, input-output units and the likes disclosed to a public. The computer programs which regulate all procedures for isolation and purification of DNA, are installed in said process control unit, and which may be programmed in common process control software commercialized.

BRIEF DESCRIPTION OF THE DRAWINGS

The above object and other advantages of the present invention will become more apparent by describing in detail a preferred embodiment thereof with reference to the attached drawings, in which.

BEST MODE FOR CARRYING OUT THE INVENTION

Hereinafter, the present invention will be described in detail with reference to the accompanying drawings.

Figure 1:
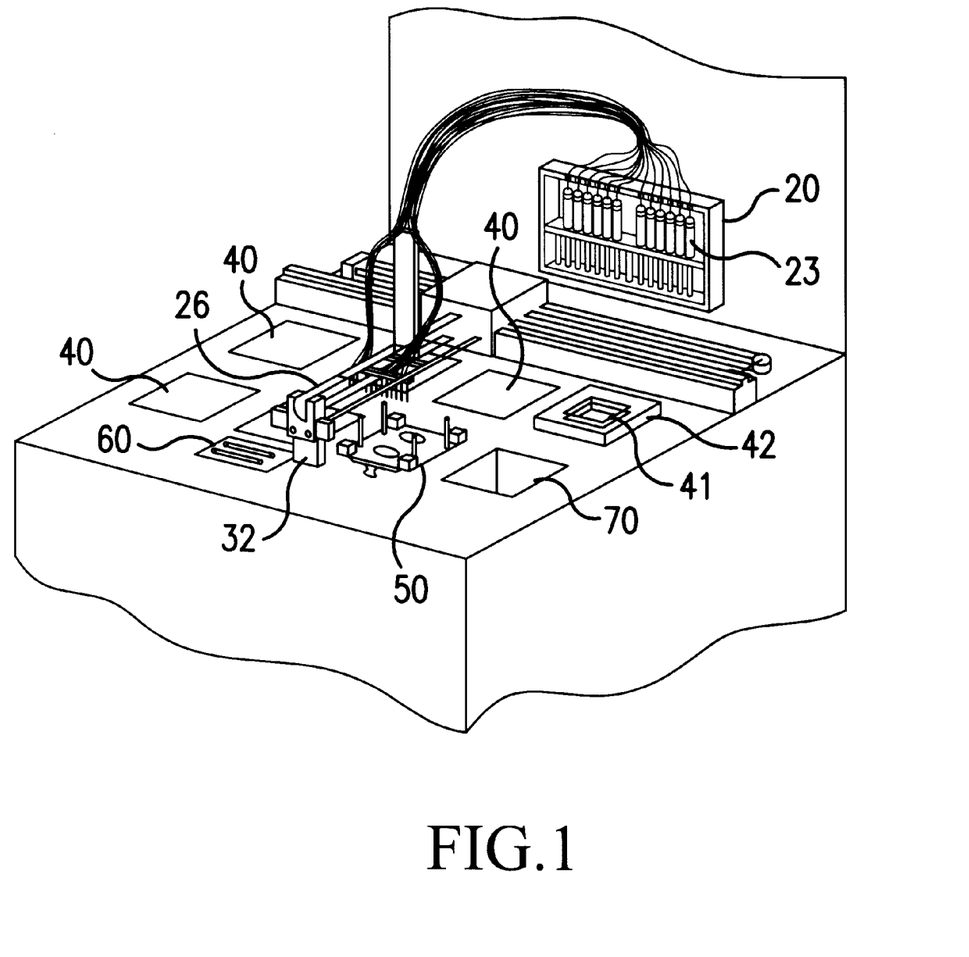
FIG. 1 is a perspective view of principal part of the automatic DNA purification apparatus of the present invention.

FIG. 1 is a perspective view of principal part of the automatic DNA purification apparatus of the present invention.

Said liquid container (10) is located in lower part of this apparatus, and comprises various bottles which store various liquids which contain DNA, such as cell culture media; lysis buffer; binding buffer (for DNA adsorption); washing buffer; elution buffer (for DNA desorption); distilled water and washing solution, and comprises bottles which hold the solutions excreted from vacuum block.

Figure 5A:
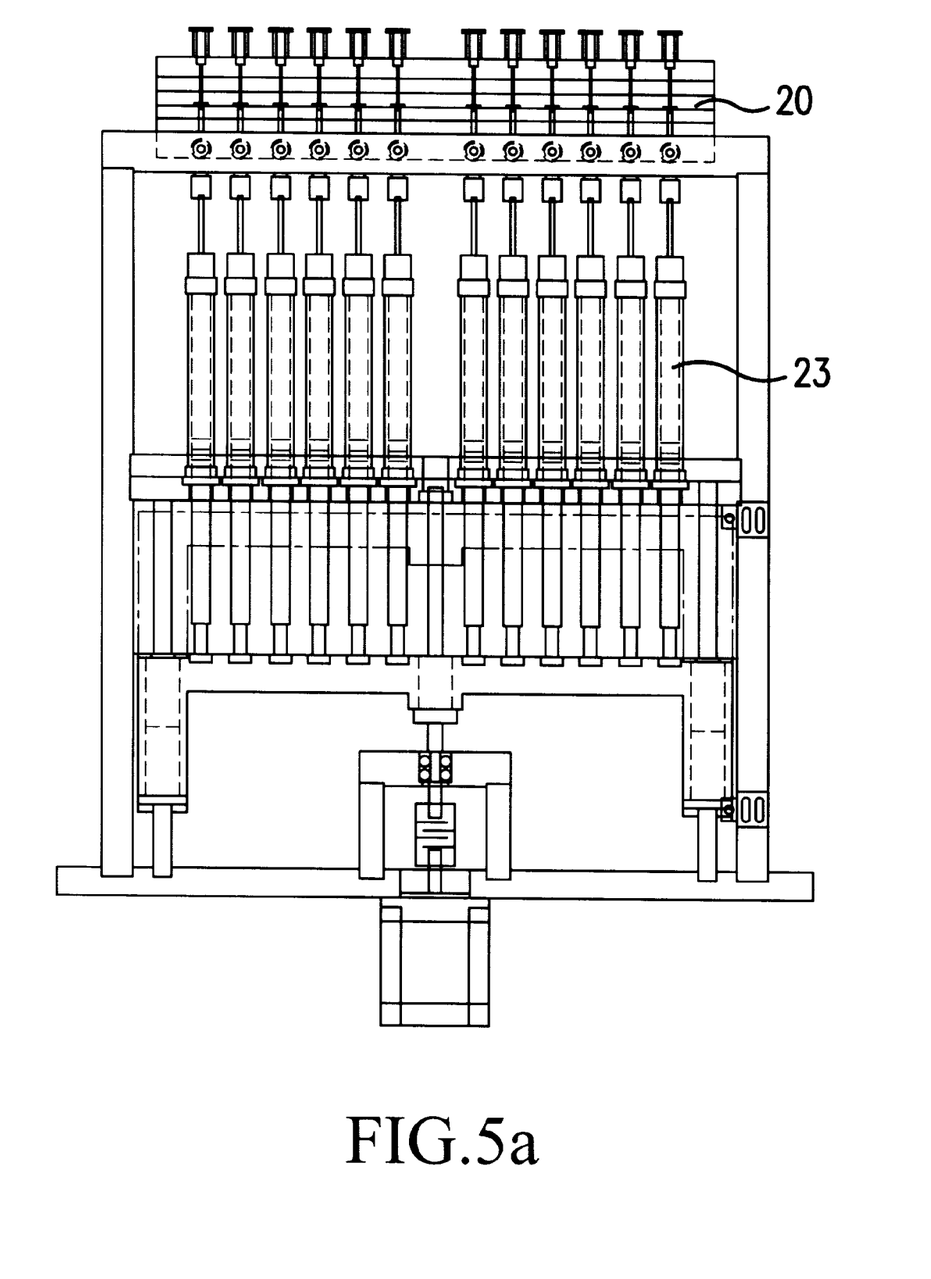
FIG. 5a is a front view of liquid control valve apparatus of the automatic DNA purification apparatus of the present invention.

Liquid control valve apparatus (20), as illustrated in FIG. 5a in detail, is connected with said liquid container (10) through liquid flow passage (21), and comprises the first control valve (22) which control the transfer of liquid through said liquid flow passage (21); syringes (23) which intake or discharge liquid quantitatively through above passage (21) by means of piston action; the second control valve (24) which blocks a backward flow of liquid discharged from syringe (23), toward said liquid container; injection needles (26) which inject liquids which have been transferred from above syringes (23) into each well of multi-well plate; and the third control valve (25) which regulate liquid flow between said syringes (23) and injection needles (26).

Upon opening of the first control valve (22), the liquids are supplied through passages from liquid container (10), and however, cannot be intaked into the syringes because the second control valve (24) is closed a this time. Then, upon opening of the second control valve (24) and closing of the first control valve (22), liquid is intaked quantitatively into syringes (23) by piston action which is driven by motor. Said syringes (23) are connected with each injection needles respectively through numerous passages (21b) and the third control valve. Said liquids which have been intaked quantitatively into syringes, are discharged from syringes quantitatively by piston action which is driven by motor, and then, transferred to said injection needles through the third control valve, and do not flow backward toward liquid container (10) due to the closing of the second control valve.

The liquids thus transferred are injected simultaneously into each well of said multi-well plate through injection needles (26). As explained above, the amounts of liquids added into each well can be controlled to an extent of 1 $\mu l$ range by using the syringes with piston driven by motor. In addition, syringe (23) can be used for washing injection needles (26) with washing buffer or washing solution by repeating intake and discharge of the above buffer or solution and in addition, can be used for mixing various liquids which are different from each other by means of repeated piston actions.

Figure 5B:
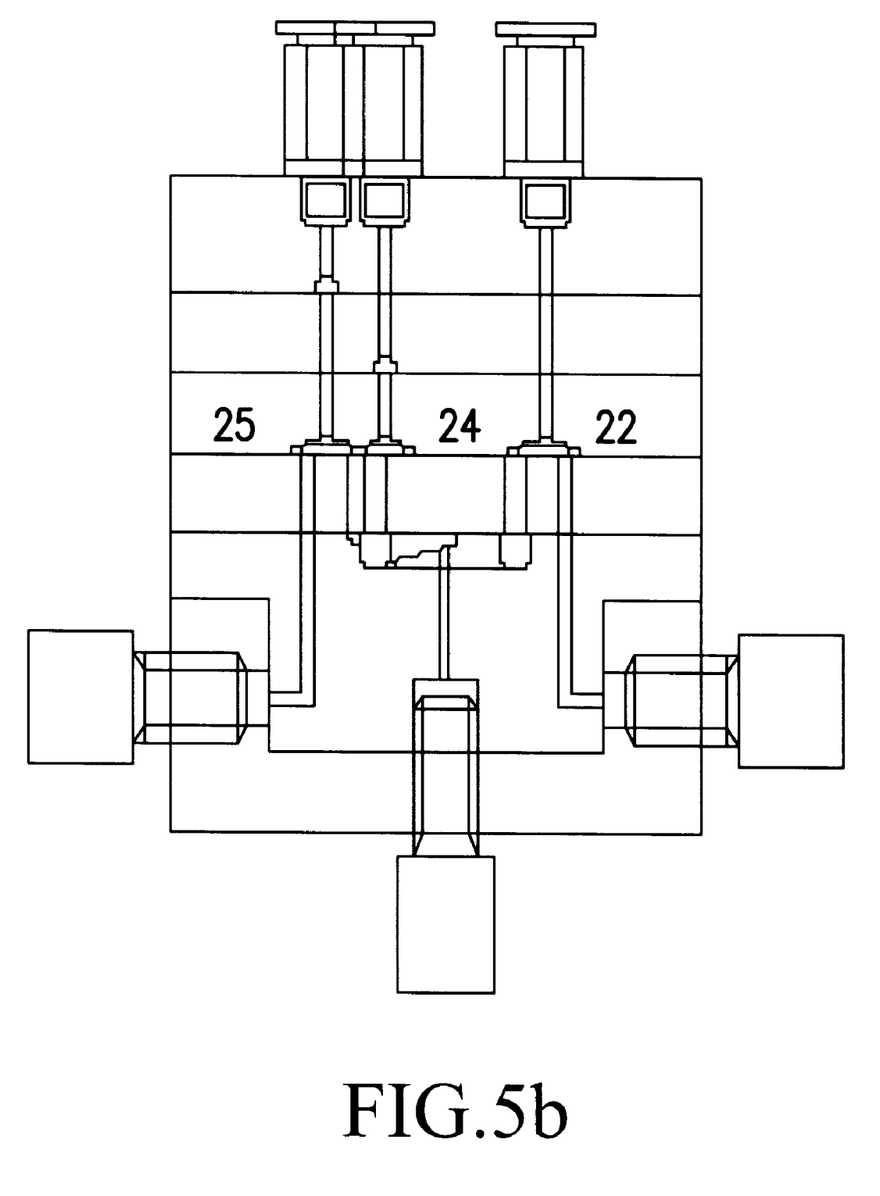
FIG. 5b is a sectional view of control valve of the automatic DNA purification apparatus of the present invention.

FIG. 5b is a sectional view of said control valve apparatus and illustrates a cross-sectional view of the first control valve (22) which regulates the supply of liquids into syringes from liquid container (10) through liquid flow passages; of the second control valve (24) which blocks backward flow of liquids between syringes (24) and the first control valve; and of the third control valve (25) which regulate liquids flow between syringes and injection needles.

The above control valve apparatus is composed of the combination of several channel block. In inner space of each channel block, three valve rooms are formed wherein membranes are disposed. Air flow passages are connected with each valve rooms. Air pressure is applied to said valve room through said air flow passages to expand said membranes and thereby closing said liquid flow passages.

Said liquids are supplied through said liquid flow passages from the liquid container (10). The flows of liquids toward syringes and injection needles, are selectively controlled through the first control valve (22), the second control valve (24) and the third control valve (25). Various kinds of solenoid valve may be employed as the control valves of the apparatus of the present invention. Preferably, the multi-channel quantitative control valve apparatus described in detail in Korea Patent Application No. 10-2000-0055968 may be employed as the control valves of the apparatus of the present invention.

The multi-well plates transported into multi-well plate block through rack (31), comprise multi-well plate which contains cell culture media, the first filter plate (trapping filter plate) for filtering cell lysate, the second filter plate (binding filter plate) for adsorbing DNA, and the recovering filter plate for recovering DNA from the second filter plate.

The standard multi-well plate, such as 96(12×8) well plate now in the market, can be used as a multi-well plate of the present invention. The wells disposed in these multi-well plates, may be cylindrical tubes generally used in DNA isolation and purification procedure. Said trapping filter or binding filter is mounted on the lower part of inside of said well of which bottom contains vacuum suction hole which can be connected with vacuum pump so that vacuum filtration can be proceeded thereby.

The trapping filter mounted on the first filter plate does not allow the permeation of cell lysate liquid under normal pressure, and however, under centrifugation or in vacuo, allows the permeation of liquid which contains plasmid DNA and retains proteins, genomic DNA, cell debris and the likes. The conventional hydrophobic filters which have been generally known as having above-mentioned functions, may be employed as a trapping filter of the present invention. Preferably, the multi-layer trapping filter described in detail in Korea Patent Application No. 10-2000-0054999, which comprises polyolefin filter layers and glass filter layer of which surface has been treated to have hydrophobicity, may be employed as a trapping filter of the present invention.

The binding filter mounted on the second filter plate is multi-layer filter which comprises the layer (DNA adsorption layer) which adsorb plasmid DNA selectively in the presence of chaotropic salts and the layer which does not allow the permeation of liquid which contains DNA under normal pressure. Said DNA adsorption layer adsorb plasmid DNA selectively in the presence of chaotropic salts and however, desorbs plasmid DNA in elution buffer as like Tris-HCl solution. Said binding filter does not allow permeation of the solution under normal pressure, and however, allow permeation of the solution under centrifugation or in vacuo. The conventional filters which have been generally known as having above-mentioned function, may be employed as a binding filter of the present invention. Preferably, the multi-layer binding filter described in detail in Korea Patent Application No. 10-2000-0054999, may be used as a binding filter of the present invention.

Figure 2:
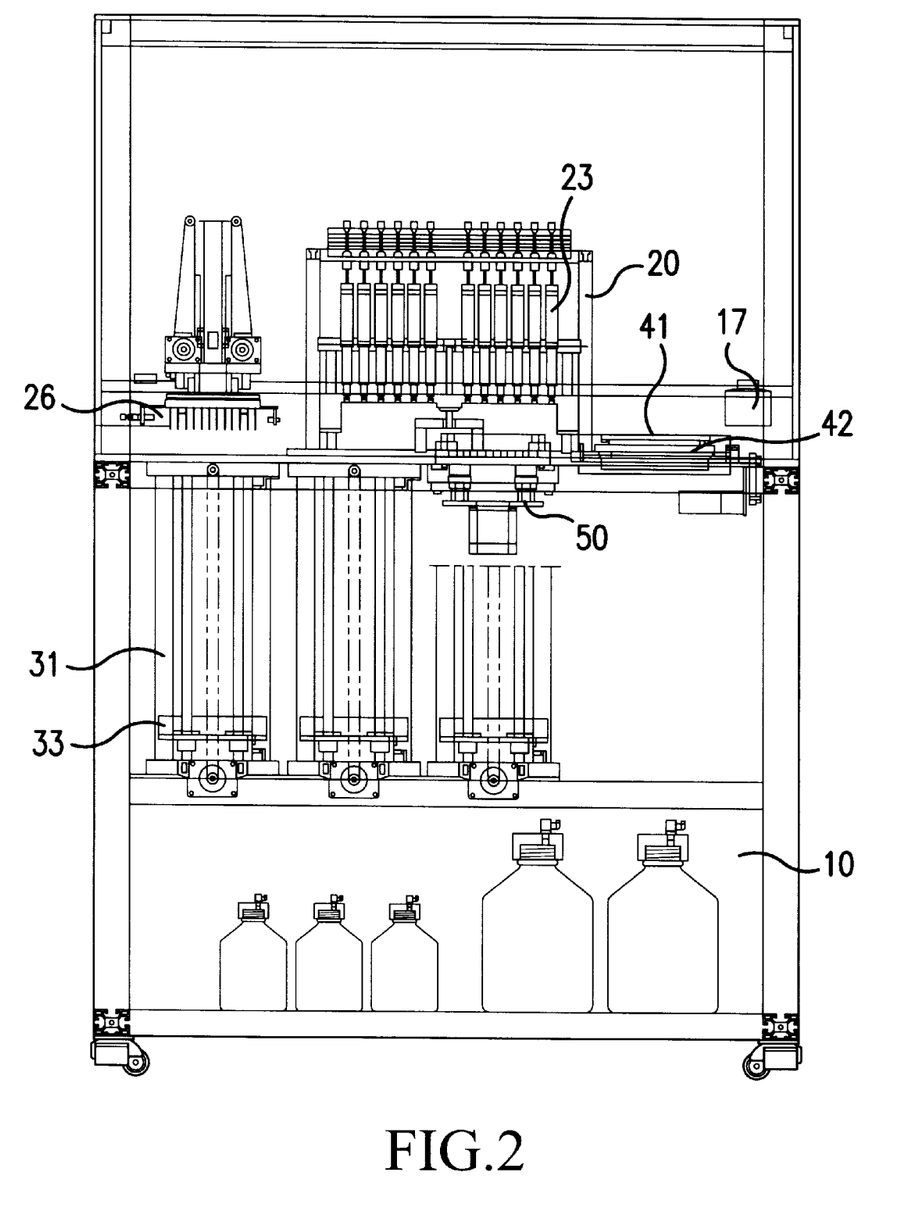
FIG. 2 is a front view of the automatic DNA purification apparatus of the present invention.
Figure 3:
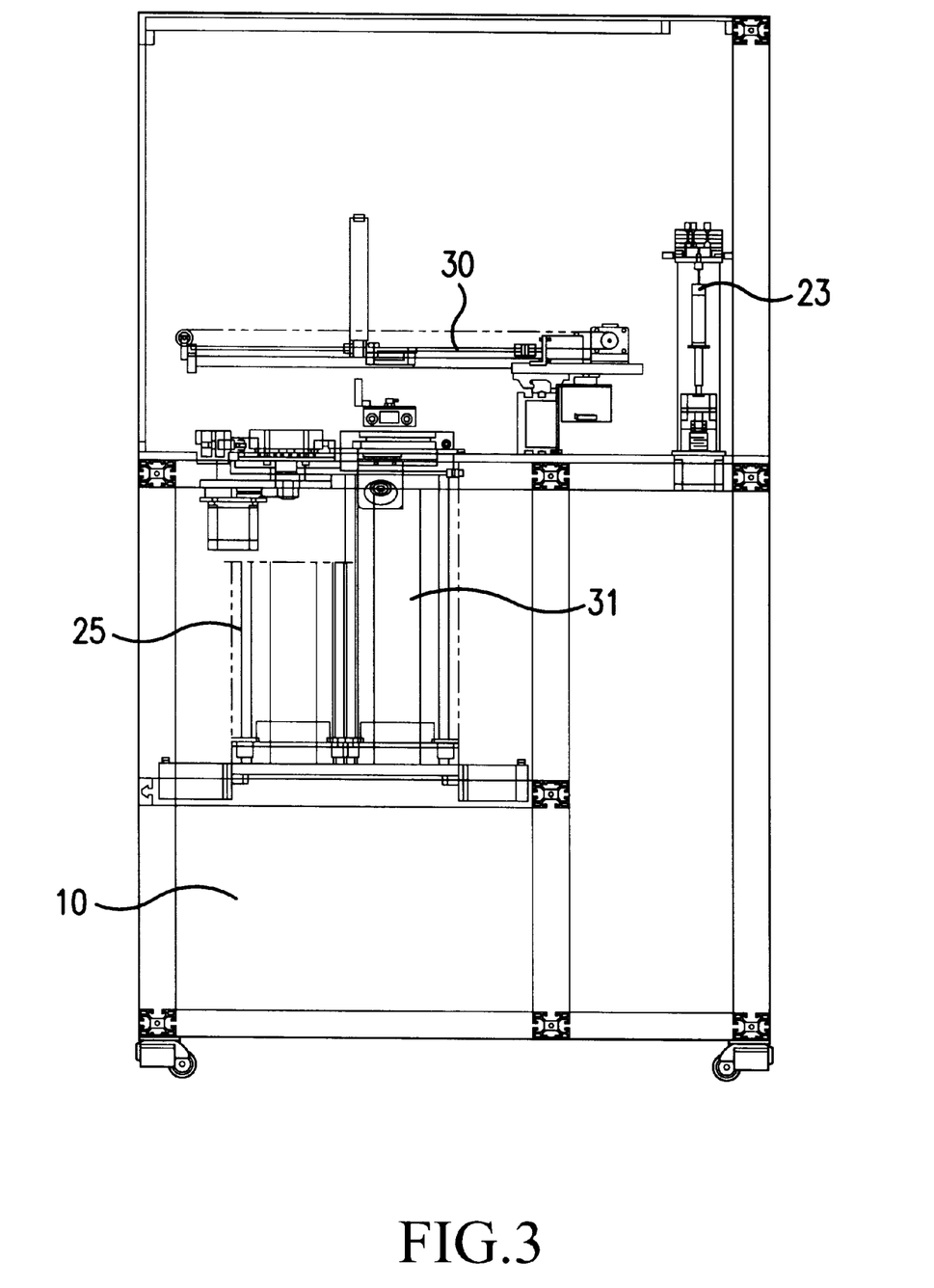
FIG. 3 is a side view of the automatic DNA purification apparatus of the present invention.

The apparatus of the present invention comprises rack (31) and chucking arm (32) which transport multi-well plate. Rack (31), as depicted in FIG. 2, comprises numerous plate table (33) on which multi-well plate is laid and table transportation means which transports plate tables (33) toward up-down direction. Said table transportation means comprises timing belts; shaft mounted on both sides of said timing belts; ball bush; and motor equipped in lower side thereof. Said rack transports multi-well plates laid on plate tables into multi-well plate block (40) by moving said plate table (33) driven with rotating shaft.

Various liquids are added, through said injection needles, into each well of multi-well plate which has been transported into multi-well plate block through said rack (31). Said chucking arm (32) transports multi-well plate thus treated, into shaking block (50) or vacuum block (41) by chucking multi-well plate and moving toward up-down and right-left directions. In addition, a vacuum pad which catches plate covers with suction and remove them from plates, is mounted on the chucking arm (32).

Figure 4:
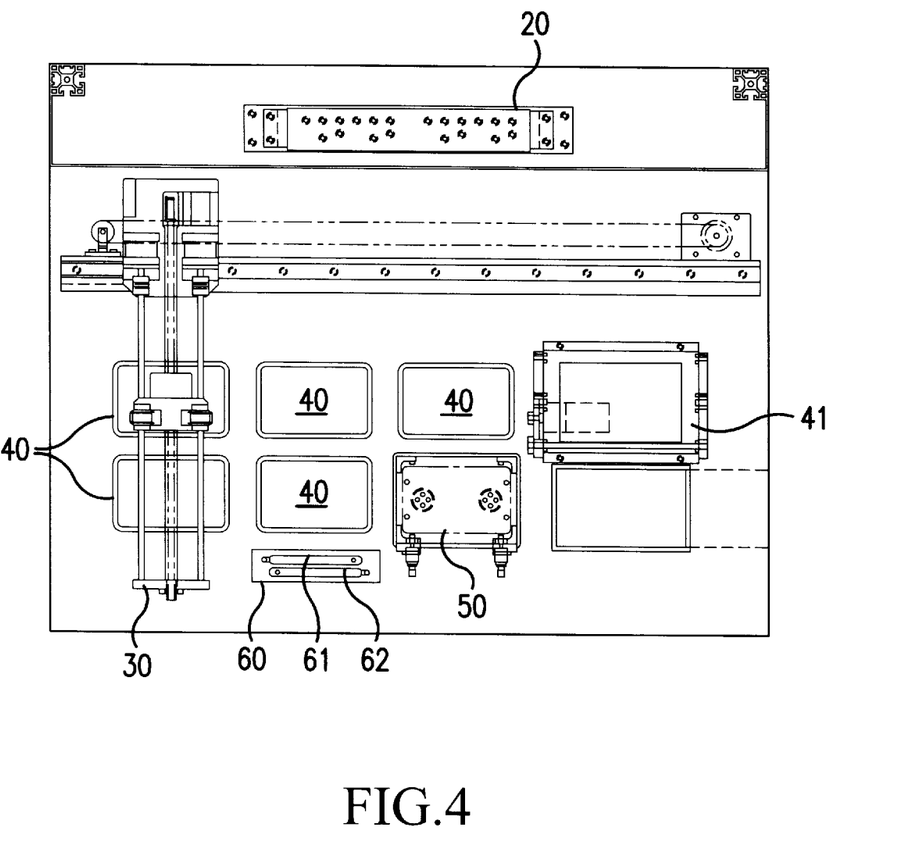
FIG. 4 is a plane view of the automatic DNA purification apparatus of the present invention.

As illustrated in FIG. 4, said transportation mean relocates said injection needles and chucking arm toward up-down (Z-axis), left-right (X-axis) and front-back (Y-axis) directions. Linear motion guides, timing belts and stepping motors are equipped along with each directions, which relocate injection needles and chucking arm. One pair of ball spline is equipped on both sides of linear motion guide of Y-axis for moving in Z-axis. A connecting bracket is mounted on said linear motion guide of Y-axis in the direction of Z-axis. Two timing belts are mounted on both sides of said connecting bracket. Injection needles and chucking arm (32) are mounted separately on said connecting bracket. Injection needles and chucking arm are relocated independently by rotation of said ball spline driven with motor.

Vacuum block (41) comprises vacuum container (42) of which bottom contains vacuum suction hole and a cover which can covers only the edge of top of said vacuum container. Said vacuum suction hole is connected with vacuum pump (not depicted) and reduced the pressure of said vacuum container by vacuum suction. Said cover of vacuum block driven with motor, seals up the edges of multi-well plates which are disposed in vacuum container with the edge of top of said vacuum container.

As illustrated in FIG. 4, washing block (60) employed optionally in the apparatus of the present invention for the rinsing of injection needles, comprises sterilizer zone (61) wherein sterilizing solution is flow and washing zone (62) wherein distilled water is flow. Also, the apparatus of the present invention may further comprise draw off duct which dump out the multi-well plates and covers thereof after using to outside of the apparatus.

The procedure of DNA isolation and purification from various biological samples using the apparatus of the present invention is as follows.

Through injection needles (26), various biological liquid samples which contain DNA are transferred to the first filter (trapping filter) plate. The second filter plate (trapping plate) is disposed in lower part of inside of vacuum container (42). The first filter plate (binding plate) is disposed over the second filter plate. Then, vacuum block (41) is operated to filter in vacuo the liquids contained in the first filter plate. Cell debris, proteins, genomic DNA and the like are retained within the first filter plate and liquids which contain plasmid DNA are collected into the second filter plate.

The binding buffer solution which contains chaotropic salts is injected to the second filter plate containing the plasmid DNA solution through injection needles in order to adsorb DNA with binding filter layer of the second filter plate. The plasmid DNA thus adsorbed on binding filter layer, is washed with washing buffer for several times and then, dried as it is adsorbed on binding filter mounted in vacuum block.

Then, the recovering filter plate is disposed in lower part of inside of vacuum container (42). The second filter plate which contains plasmid DNA thus dried, is disposed over said recovering filter plate. Through injection needles (26), elution buffer such as Tris-HCl solution are injected into each well of the second filter plate in order to desorb plasmid DNA from binding filter. Then, vacuum block (41) is operated to collect purified plasmid DNA into the recovering plate.

INDUSTRIAL APPLICABILITY

The automatic DNA purification apparatus of the present invention comprises the multi-channel quantitative control valve apparatus which is constituted by numerous syringes and control valves and thus, can isolate and purify plasmid DNA simultaneously from various biological samples. In addition, the apparatus of the present invention can curtail the consumptive material cost for DNA isolation and purification process by employing the injection needle which can be washed as it is mounted and can be used repeatedly in lieu of the conventional disposable injection tip. Further, the apparatus of the present invention can isolate and purify high purity DNA in a large amount within a short time from various liquids which contain DNA as like cell culture media by means of continuous feeding of DNA containing liquid through plate transportation means and rack wherein numerous plate are arranged and transported sequentially and, by means of the completely automated procedure through a continuous and automatic mounting of the plates in vacuum block.

In conclusion, the apparatus of the present invention can automate completely the conventional hand-worked process for isolation and purification of DNA, which is most frequent and prerequisite step for gene manipulation.

While the present invention has been particularly shown and described with reference to particular embodiments thereof, it will be understood by those skilled in the art that various changes in form and details may be effected therein without departing from the spirit and scope of the invention as defined by the appended claims.

What is claimed is:

1. An automatic DNA purification apparatus, which comprises:
   a plurality of liquid containers (10) which supply various liquid reagents and DNA containing solutions;
   a first set of liquid flow passages (21) connected to said liquid containers wherein said liquid reagents stored in said liquid containers (10) are conveyed;
   a plurality of control valves (22, 24, 25) of which the first control valve (22) controls the transfer of liquid through a first set of liquid flow passages, the second valve (24) blocks a backward flow of liquid discharged from syringes (23) toward the liquid containers, and the third control valve (25) regulates liquid flow between said syringes and injection needles (26);
   a plurality of syringes (23) connected to said first set of liquid flow passages which intake and discharge quantitatively said liquid reagents, the movement of the pistons connected to said plurality of syringes being controlled by said third control valves;
   a second set of liquid flow passages connecting said plurality of syringes to a plurality of injection needles (26);
   transporting mean (30) for moving said plurality of injection needles and/or multi-well plate toward up-down and/or right-left directions and/or in a back and forth direction;
   a vacuum block (41) wherein liquids contained in said multi-well plate are filtered in vacuum;
   a plurality of multi-well plate racks (31) which transports said multi-well plates towards up-down directions;
   a plurality of multi-well plate blocks (40) wherein multi-well plates transported by said multi-well plate rack, are mounted;
   a process control unit which regulates the operation of said control valves for selection and transfer of said liquid reagents, the operation of said plurality of syringes for quantitative intake and discharge of said liquid reagents, the transfer of said injection needle connected with said syringes among multi-well plate blocks, the sequential transportation of said multi-well plates arranged in said multi-well plate rack, and the operation of said vacuum block, according to computer program.

2. The automatic DNA purification apparatus according to claim 1, further comprising a shaking block (50) which shakes said multi-well plate.

3. The automatic DNA purification apparatus according to claim 1 or claim 2, further comprising a washing block (60) which washes said injection needles.

4. The automatic DNA purification apparatus according to claim 3, wherein said washing block comprises a sterilizing zone and washing zone.

5. The automatic DNA purification apparatus according to claim 1, wherein said multi-well plate rack (31) comprises a plurality of plate tables (33) which convey a plurality of multi-well plates toward an up-down direction and a table transportation means which transports plate tables (33) toward an up-down direction.

* * * * *